(12) United States Patent
Ingvarsson

(10) Patent No.: US 7,429,325 B2
(45) Date of Patent: Sep. 30, 2008

(54) DEVICE FOR A BODY FLUID BAG

(75) Inventor: Henrik Ingvarsson, Onsala (SE)

(73) Assignee: Hammarplast Medical AB, Lidkoping (SE)

( * ) Notice: Subject to any disclaimer, the term of this patent is extended or adjusted under 35 U.S.C. 154(b) by 377 days.

(21) Appl. No.: 10/548,670

(22) PCT Filed: Mar. 24, 2004

(86) PCT No.: PCT/SE2004/000448

§ 371 (c)(1),
(2), (4) Date: Sep. 9, 2005

(87) PCT Pub. No.: WO2004/084792

PCT Pub. Date: Oct. 7, 2004

(65) Prior Publication Data

US 2006/0191830 A1 Aug. 31, 2006

(30) Foreign Application Priority Data

Mar. 26, 2003 (SE) .................................... 0300855

(51) Int. Cl.
B01D 29/00 (2006.01)
B01D 29/05 (2006.01)
B01D 29/11 (2006.01)
B01D 29/15 (2006.01)
B01D 29/23 (2006.01)
A61B 19/00 (2006.01)
B01D 36/00 (2006.01)

(52) U.S. Cl. .................... 210/257.1; 210/136; 210/767; 210/252; 210/435; 604/406; 604/408

(58) Field of Classification Search ....................... None
See application file for complete search history.

(56) References Cited

U.S. PATENT DOCUMENTS

| 2,848,995 | A | * | 8/1958 | Ryan | 604/406 |
| 3,492,991 | A | * | 2/1970 | Dyer, Jr. | 604/6.09 |
| 4,033,345 | A | | 7/1977 | Sorenson et al. | |
| 4,435,170 | A | | 3/1984 | Laszczower | |
| 4,466,888 | A | * | 8/1984 | Verkaart | 210/232 |
| 4,834,743 | A | | 5/1989 | Valerio | |
| 5,133,703 | A | | 7/1992 | Boehringer et al. | |
| 5,445,731 | A | * | 8/1995 | Tuohey et al. | 210/149 |
| 5,695,489 | A | * | 12/1997 | Japuntich | 604/406 |
| 6,099,734 | A | * | 8/2000 | Boggs et al. | 210/650 |
| 6,682,656 | B2 | * | 1/2004 | Rothman et al. | 210/767 |
| 2004/0243094 | A1 | * | 12/2004 | Dumon D'Ayot et al. | 604/410 |

FOREIGN PATENT DOCUMENTS

NL 1016515 7/2002

* cited by examiner

Primary Examiner—Krishnan S. Menon
Assistant Examiner—Madeline Gonzalez
(74) Attorney, Agent, or Firm—Young & Thompson

(57) ABSTRACT

A device (2) for a body fluid bag, includes a filtering part (5) and a retransfusion part (6), the filtering part (5) having a filtering part inlet opening (7) and a filtering part outlet opening (8). The outlet opening (8) is arranged to be connected to an inlet opening of the body fluid bag, and the retransfusion part (6) has a retransfusion part inlet opening (10), being arranged to be connected to an outlet opening of the body fluid bag, and a retransfusion part outlet opening (11), wherein the filtering part (5) and said retransfusion part (6) are mechanically integrated to form a single unit. A transfusion unit (16) including such a device (2) is also disclosed.

12 Claims, 3 Drawing Sheets

DEVICE FOR A BODY FLUID BAG

TECHNICAL FIELD OF THE INVENTION

This invention relates to a device for a body fluid bag, the device comprising a filtering part and a transfusion part. The invention also relates to a transfusion unit, comprising such a device.

BACKGROUND OF THE INVENTION

During for example surgery, such as chest cavity surgery, a patient usually loses large amounts of blood. One way of dealing with this problem is to remove the lost blood and give the patient a transfusion of donated blood, to make up for the lost blood. Such donations are however accompanied with a plurality of problems, such as rejection of the donated blood, and the risk for spreading diseases.

In order to overcome these problems, it has been proposed in the prior art to collect blood lost from the patient and return this blood to the circulatory system of the patient. This is referred to as autologous blood transfusion. A transfusion unit according to the prior art is disclosed in FIGS. 1a and 1b. This transfusion unit comprises a blood bag, which has an inlet in an upper part of the bag and an outlet in the lower part of the bag. Within the blood bag, a main filter is integrated, so that blood that is entered into the blood bag is filtered. This filtration is essential in autologous blood transfusion, since it removes impurities, such as thrombi and tissue fragments in a wound. After filtration, the blood is collected in the bottom of the blood bag until it is to be retransfused. In this collection position (FIG. 1a), the outlet from the bag is blocked by means of a clamp or the like. When the blood is to be retransfused (FIG. 1b), a transfusion set is connected to the outlet of the bag. Thereafter the clamp is removed, and the transfusion set filter is primed and all air is expelled from the tubing before the transfusion set being connected to a cannula or the like in the patient and blood is retransfused into the patient. The transfusion set may be equipped with a blood filter in order to remove any blood clots or the like which may develop when storing the blood in the blood bag.

However, the prior art device described above have a plurality of disadvantages. First, the main filter is integrated in the blood bag, which means that only special blood bags may be used for this purpose. Moreover, these blood bags are quite complicated, and hence quite costly to manufacture. Moreover, as the blood bag is filled with blood, there is a risk that the level of blood may rise so that the stored blood is in contact with the filter while stored, which may decrease the quality of the stored blood.

SUMMARY OF THE INVENTION

Hence, an object of this invention is to overcome the above mentioned problems with the prior art.

The above and other objects are at least in part achieved with a device for a body fluid bag, the device comprising a filtering part and a retransfusion part, the filtering part having a filtering part inlet opening and a filtering part outlet opening, the outlet opening being arranged to be connected to an inlet opening of said body fluid bag, and the retransfusion part having a retransfusion part inlet opening, being arranged to be connected to an outlet opening of said body fluid bag, and a retransfusion part outlet opening, wherein said filtering part and said retransfusion part are mechanically integrated to form a single unit. Hence, according to the invention, regular blood bags, which may be manufactured at low cost, may be used for autologous blood transfusion. Moreover, since the filtering part is separated from the blood bag, there is no risk for the filter affecting the blood quality, when the blood has entered the blood bag. Also, the inventive solution is flexible, and blood bags of different materials, sizes and designs may be used.

Suitably, the device further comprises a check valve arranged in proximity with the filtering part outlet opening, in order to allow a flow of filtered body fluid in the direction from the filtering part to the fluid bag and to hinder a flow in the opposite direction. This prevents that blood is re-entered into the filter once it has entered the blood bag from the filter.

Moreover, said retransfusion part comprises an integrated drip chamber, in order to control a flow of body fluid out from said retransfusion part outlet opening. Suitably, said retransfusion part also comprises a retransfusion filter, arranged up-stream said drip chamber, for filtering for example blood clots that may arise in the blood bag.

Suitably, the filtering part comprises a housing, into which said filtering part inlet and outlet openings are emanating, and a filter being arranged in said housing, whereby said inlet and outlet openings are arranged at essentially opposite sides of said housing in order to provide a sufficiently long flow path for said body fluid through the filter in said housing, enabling good filtration of the body fluid.

The above and other objects of the invention are also at least in part achieved by a transfusion unit comprising a body fluid bag, having a bag inlet opening and a bag outlet opening, and a device as defined above, having a filtering part outlet opening and a retransfusion part inlet opening, said filtering part outlet opening being connected to the bag inlet opening and the retransfusion part inlet opening being connected to the bag outlet opening. By the inventive arrangement, a unit is provided that is simple to use and may be manufactured cost-efficiently. The inventive arrangement also provides for a solution in which the parts needed for retransfusion is included in the device, and the unit may be sterilised as a unit, resulting in a hygienic solution. Suitably, said body fluid bag is a flexible bag, for example a bag of a plastic material.

The above and other objects of the invention are also at least in part achieved by a method for collection and retransfusion of blood, comprising the following steps: (a) providing a transfusion unit as defined above, (b) connecting the filtering part inlet opening to a source of a body fluid to be collected, (c) collecting said body fluid in said body fluid bag, (d) when the body fluid is to be retransfused, turning the body fluid bag and placing it so that body fluid can flow into the bag outlet opening and so that the body fluid is allowed to flow into the retransfusion part, whereafter a flow of body fluid may be established through the retransfusion part outlet opening, out of said transfusion unit. A drip chamber may be arranged downstream the bag outlet opening.

BRIEF DESCRIPTION OF THE DRAWINGS

The invention will hereinafter be described in closer detail by means of preferred embodiments thereof, with reference to the accompanying drawings.

FIG. 3 is a schematic cross-section drawing of a detail of the inventive transfusion unit as disclosed in FIG. 2a.

DESCRIPTION OF PREFERRED EMBODIMENTS

Figure 1A:
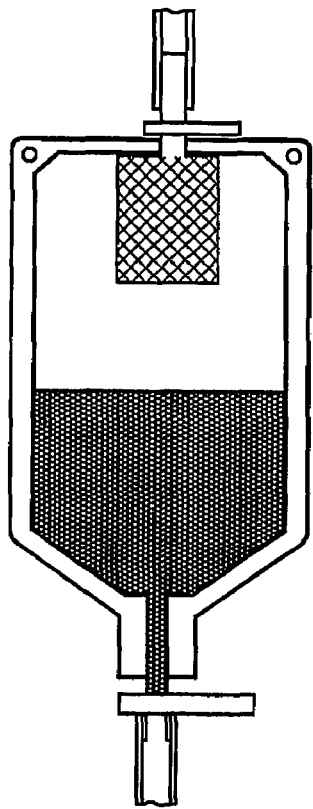
FIG. 1a is a schematic cross-section drawing of a transfusion unit according to the prior art, as seen in a collection position.
Figure 1B:
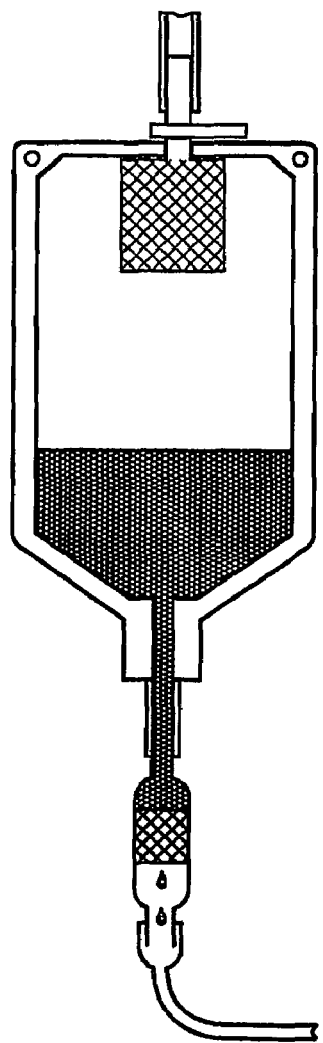
FIG. 1b is a schematic cross-section drawing of the transfusion unit in FIG. 1a, as seen in a retransfusion position.
Figure 2A:
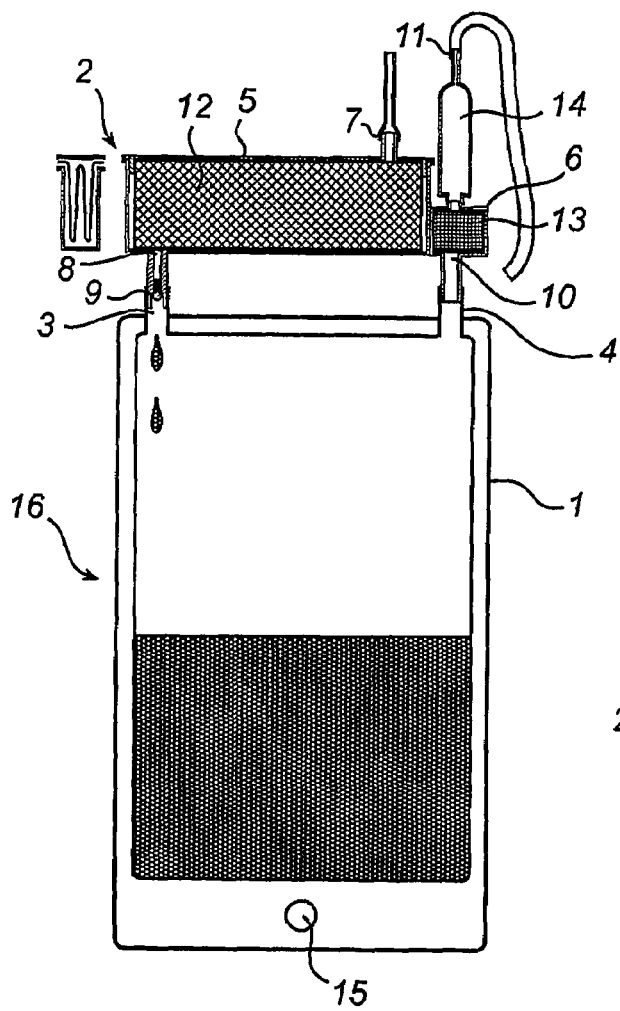
FIG. 2a is a schematic cross-section drawing of a transfusion unit according to the invention, as seen in a collection position.
Figure 2B:
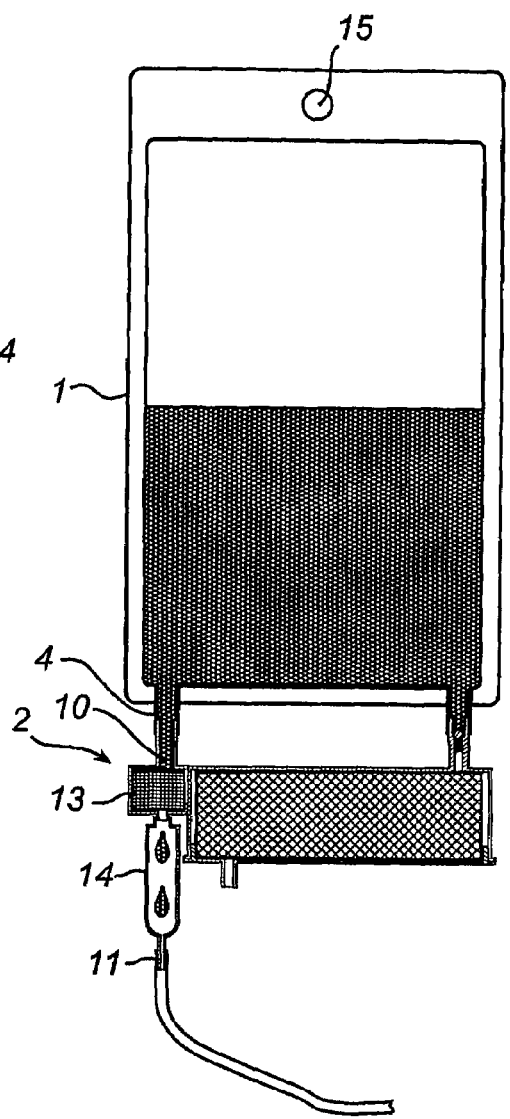
FIG. 2b is a schematic cross-section drawing of the inventive transfusion unit in FIG. 2a, as seen in a retransfusion position.
Figure 3:
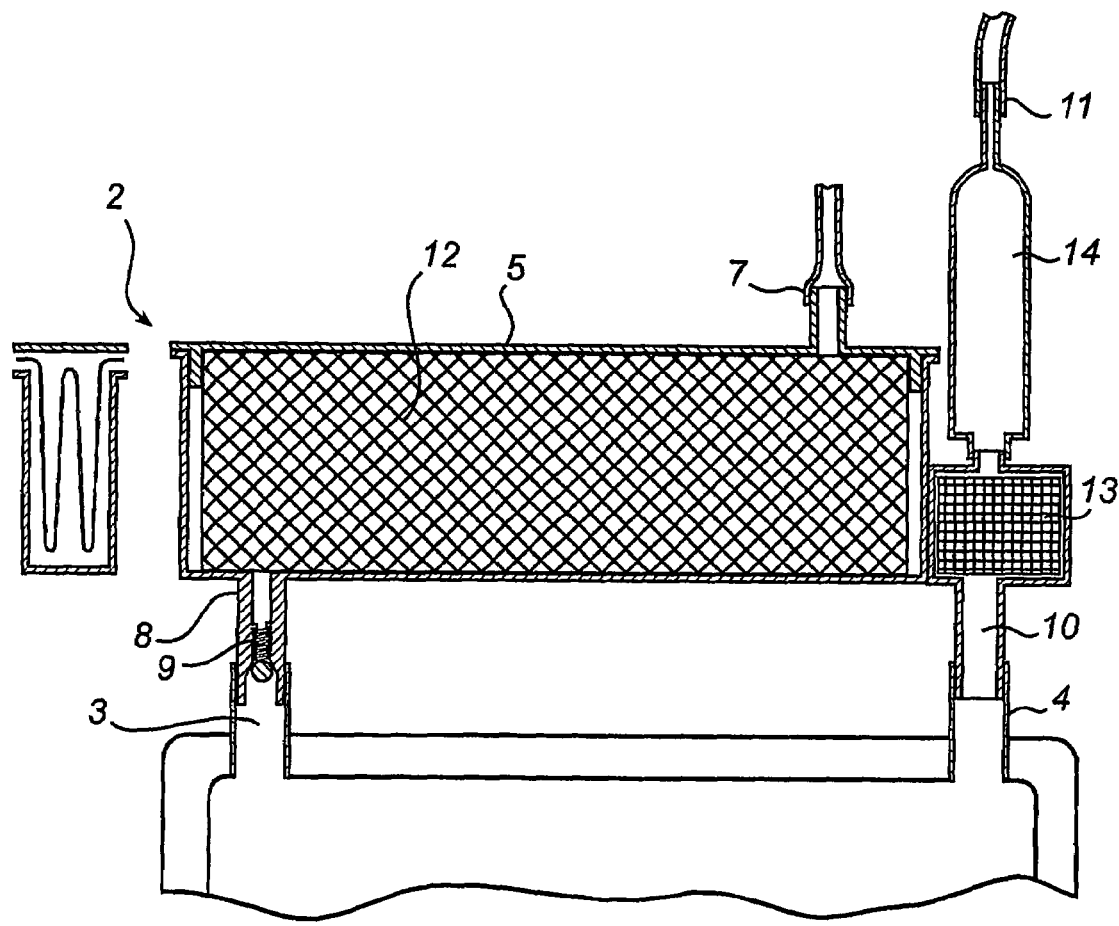

FIG. 2a, FIG. 2b and FIG. 3 discloses a first embodiment of this invention. With reference to FIG. 2a and FIG. 3, a transfusion unit 16 is disclosed in a first, collection position. FIG. 2b shows the transfusion unit 16 in a retransfusion position. The transfusion unit 16 essentially comprises a body fluid bag 1, such as a bag for collecting blood or plasma, the bag 1 being manufactured from a flexible material, such as a plastic material. In the present example, the body fluid bag 1 is a blood bag, for collection of blood. The transfusion unit 16 also comprises an integrated filtering device 2, which will be described in closer detail below.

The integrated filtering device 2 is essentially subdivided into a filtering part 5 and a retransfusion part 6, said parts being integrated into a single mechanical component, which is connected to the blood bag 1.

The filtering part 5 of the filtering device 2 essentially comprises a filtering part inlet opening 7, which may be connected to a source of blood, for example a patient or a donor, a filter 12, and a filtering part outlet 8, which is connected to a bag inlet opening 3 on said blood bag 1. The filter 12 is a mechanical filter, which may or may not be coated with an active substance, such as antibodies, in order to allow filtration of leukocytes, lipids and undesired proteins. Moreover, the filter material and structure may be chosen to suit the desired purpose. As is indicated in FIG. 2a, the filter may be folded one or more times within the filtering part 5, in order to increase the filtering area of the filter. Furthermore, a check valve 9 is provided between the filtering part outlet 8 and the bag inlet opening 3, the check valve 9 serving to allow flow only from the filtering part 5 to the blood bag 1.

The retransfusion part 6 of the filtering device 2 essentially comprises a retransfusion part inlet opening 10, which is connected to a blood bag outlet opening 4 of said blood bag 1, a retransfusion drip chamber 14 and a retransfusion part outlet opening 11, which is arranged to be connected to a recipient of the retransfused blood, such as a patient or a collecting device or the like. The retransfusion part 6 may also comprise an additional retransfusion filter 13, being arranged upstream said retransfusion drip chamber. This retransfusion filter 13 may be used to filter out for example blood clots which may arise when storing blood collected in said blood bag 1.

The function of the above described transfusion unit 16 will hereinafter be described.

When blood is to be collected from a blood source, a flow channel, such as a tube, is connected between said blood source and said inlet opening 7 of said filtering part 5. When blood is to be collected, the transfusion unit is in the position disclosed in FIG. 2a. Blood is thereafter drained from said blood source and is transferred to the transfusion device, via said filtering part inlet opening 7, by means of pressure (Means for generating said pressure is not disclosed in the present drawings). Alternatively, a pump may be used to transfer blood into the transfusion unit 16, via said filtering part inlet opening 7. By means of gravity, the blood is thereafter transported through the filter 12 of the filtering part 5 of the filtering device 2, whereby particles present in the blood, such as thrombi, tissue fragments or the like is filtered away. According to an embodiment of the invention described above, in which the filter is coated with an active substance, such as antibodies, also blood components such as leukocytes, lipids, undesired proteins and other inflammatory chemical mediators of cytokines, may be filtered away. Once filtered, the blood flows through the filtering part outlet opening 8, the check valve 9 and the bag inlet opening 3, into the blood bag 1, in which the blood may be stored until it is to be used.

When the blood stored in the blood bag is to be used, for example retransfused into a patient, which may or may not be the same as the donor or blood source, the transfusion unit 16 is placed so that blood can pass through the retransfusion part 6 and the drips in the drip chamber fall vertically, as indicated by FIG. 2b. For this purpose, a suspension opening 15 is provided in the blood bag. When the transfusion unit 16 is turned upside down, the content of the blood bag 1 is forced by means of gravity into the bag inlet and outlet openings 3, 4. A flow of blood out through the bag inlet opening 3 is prohibited by the provision of said check valve 9, which prohibits flow in that direction. Instead, the flow of blood is directed out through the bag outlet opening 4, connected with the retransfusion part inlet opening 10. First, the blood is passed through the retransfusion filter 13, which filters out any blood clots or the like which have been generated during storage of blood in the blood bag 1. Thereafter, the filtered blood is passed to the retransfusion drip chamber 14, whereafter the blood is allowed to exit the transfusion unit 16 through said retransfusion part outlet opening 11. The retransfusion part outlet opening 11 is suitably connected to a tube, which in its other end is connected to a cannula in a patient. On this tube, means for throttling the flow of blood to the patient are provided in order to provide a desired velocity of flow of blood to the patient.

As indicated above, in the present example, the filtering device 2 and the blood bag 1 are connected to each other by means of two connections, one constituted by the filtering part outlet opening 8 and the bag inlet opening 3, and the other one constituted by the bag outlet opening 4 and the retransfusion part inlet opening 10. However, it shall be noted that the invention is not to be limited to this arrangement. The main issue is that the connection between the filtering device 2 and the blood bag 1 provides for a first flow of blood between the filtering part and the blood bag when the bag is in the collection position disclosed in FIG. 2a, and a second flow of blood between the blood bag and the retransfusion part 6 when the bag is in the retransfusion position disclosed in FIG. 2b. This may however be realised with a single connection between the filtering part 2, and the blood bag 1, in which case internal flow distribution channels may be provided in the filtering device 2. The above function may also be realised with multiple connections between the filtering device 2 and the blood bag 1. In any case, said check valve 9 is arranged to prevent flow of blood into the filtering part 5, when the transfusion unit 16 is in the retransfusion position disclosed in FIG. 2b. In the case of multiple connections, multiple check valves 9 may be used to realise this function.

Also, it shall be noted that the position of the check valve 9 is not of main importance for this invention. The check valve 9 may for example be positioned within the filtering part 5, in connection with said filtering part outlet opening 8, or in the blood bag 1, in connection with said blood bag inlet opening 3. Alternative, the check valve 9 may be realised as a separate component, to be used as a connection part, when connecting the filtering part outlet opening 8 with the bag inlet opening 3. Also, it shall be noted that instead of said check valve 9, a clamp or a regular valve may be provided in the same position, in order to obtain the same function, but manually operated.

In the shown embodiment there is no fluid connection between the filtering part 5 and the retransfusion part 6, but they are only mechanically connected and integrated into a single unit constituting said filtering device 2. This mechanical integration is advantageous in that it facilitates manufacturing and simple assembly. Moreover, in most cases the transfusion unit is delivered in a state where the bag 1 is connected with the filtering device 2. This also results in easy handling, and the entire unit may be sterilised at once.

Essentially, the filtering part comprises a housing, into which said filtering part inlet and outlet openings are emanating, and a filter being arranged in said housing, whereby said inlet and outlet openings are arranged at essentially opposite sides of said housing in order to provide a sufficiently long flow path for said body fluid through the filter in said housing. The provision of said housing makes it easy to exchange the filter, and to easily manufacture transfusion units having different filter types. The housing is suitably manufactured from a plastic material, which may be sterilised. Such a housing is also suitable for automatic manufacture. Moreover, the bag used with the present invention may be of standard type, and may be provided in a cost-efficient manner.

Many modifications, improvements and variations of the above described embodiments are obvious for those skilled in the art, and such modifications, improvements and variations are intended to form part of the disclosure, and are also intended to fall within the scope and spirit of the invention as defined by the appended claims. Hence, the above description of preferred embodiments of the invention is only given by way of example, and the invention is only to be limited to what is stated in the following claims taking equivalent solutions into account. As an example, the inventive solution may be used for collection and retransfusion of other body fluids, besides blood, such as plasma.

It shall also be noted that the present invention also may be used in an alternative manner, in which the transfusion unit constantly is in the position disclosed in FIG. 2b. In that case, the body fluid is forced into the bag, via said filter, by means of pressure, and a clamp, a valve or the like may be used to regulate the flow of body fluid out of the transfusion unit.

In the shown embodiment there is no fluid connection between the filtering part 5 and the retransfusion part 6. In an alternative embodiment the retransfusion part inlet opening 10 is directly connected with a further filtering part outlet opening, which further filtering part outlet opening is arranged downstream the filter in the filtering part and situated adjacent the retransfusion part inlet opening 10. The purpose with this construction is to avoid that body fluid remains in the filtering part adjacent the retransfusion part when the body fluid bag is positioned with the filtering part outlet opening on a higher level than the retransfusion part inlet opening 10. In a further alternative embodiment the body fluid bag has a common inlet and outlet opening to which the filtering part outlet opening and the retransfusion part inlet opening are directly connected.

The used expression a body fluid bag is intended to cover a fluid bag of a flexible plastic material and also a fluid bag of stiff material.

The invention claimed is:

1. A device (2) for a body fluid bag, the device comprising a filtering part (5) and a retransfusion part (6), the filtering part (5) having a filtering part inlet opening (7) and a filtering part outlet opening (8), the outlet opening (8) being arranged to be connected to an inlet opening of said body fluid bag, and the retransfusion part (6) having a retransfusion part inlet opening (10), being arranged to be connected to an outlet opening of said body fluid bag, and a retransfusion part outlet opening (11), wherein said filtering part (5) and said retransfusion part (6) are mechanically integrated to form a single unit, and the filtering part (5) is separated from the body fluid bag; the device further comprising a non-return valve (9) arranged in proximity with the filtering part outlet opening (8), in order to allow a flow of filtered body fluid in the direction from the filtering part (5) to the fluid bag and to hinder a flow in the opposite direction.

2. A device as in claim 1, wherein said retransfusion part (6) comprises an integrated drip chamber (14), in order to control a flow of body fluid out from said retransfusion part outlet opening (11).

3. A device as in claim 2, wherein said retransfusion part (6) comprises a retransfusion filter (13), arranged up-stream said drip chamber (14).

4. A device as claimed in claim 1, wherein the filtering part (5) comprises a housing, into which said filtering part inlet and outlet openings (7,8) are emanating, and a filter (12) being arranged in said housing, whereby said inlet and outlet openings (7,8) are arranged at essentially opposite sides of said housing in order to provide a sufficiently long flow path for said body fluid through the filter in said housing.

5. A transfusion unit comprising a body fluid bag (1), having a bag inlet opening (3) and a bag outlet opening (4), and a device (2) as defined in claim 1, having a filtering part outlet opening (8) and a retransfusion part inlet opening (10), said filtering part outlet opening (8) being connected to the bag inlet opening (3) and the retransfusion part inlet opening (10) being connected to the bag outlet opening (4).

6. A transfusion unit according to claim 5, wherein said body fluid bag (1) is a flexible bag of a plastic material.

7. Method for collection and retransfusion of blood, comprising the following steps: (a) providing a transfusion unit as defined by claim 5, (b) connecting the filtering part inlet opening (7) to a source of a body fluid to be collected, (c) collecting said body fluid in said body fluid bag (1), (d) when the body fluid is to be retransfused, turning the body fluid bag up- side-down, so that the body fluid is allowed to flow into the retransfusion part (6), whereafter a flow of body fluid may be established through the retransfusion part outlet opening (11), out of said transfusion unit.

8. A transfusion unit according to claim 5, wherein the transfusion unit is configured for autologous blood transfusion.

9. A transfusion unit according to claim 5, wherein the transfusion unit is configured for blood transfusion from a donor to a recipient.

10. A device as in claim 1, wherein the filtering part (5) comprises a filter (12) coated with an active substance.

11. A device as in claim 10, wherein the filter (12) coated with an active substance is adapted to remove leucocytes, lipids, undesired proteins or chemical mediators of cytokines.

12. A device as in claim 10, wherein the active substance comprises antibodies.

* * * * *